US00PP33763P2

(12) United States Plant Patent
Hansen

(10) Patent No.: US PP33,763 P2
(45) Date of Patent: Dec. 21, 2021

(54) ***DIGITALIS* HYBRID PLANT NAMED 'FLAMINGO'**

(50) Latin Name: ***Digitalis* x *(digitalis* x *Isoplexis)***
Varietal Denomination: Flamingo

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,428

(22) Filed: Jun. 29, 2021

(51) Int. Cl.
*A01H 5/02* (2018.01)
*A01H 6/68* (2018.01)

(52) U.S. Cl.
USPC ..... Plt./263.1
CPC ..... *A01H 6/68* (2018.05)

(58) Field of Classification Search
USPC ..... Plt./263.1
CPC ..... A01H 5/02
See application file for complete search history.

*Primary Examiner* — Kent L Bell

(57) ABSTRACT

The new and distinct cultivar of *Digitalis* intergeneric hybrid plant named 'Flamingo' is characterized by sturdy, upright and dense habit with dark-green, serrate foliage and densely-branched flower stems with flowers that are open-faced, campanulate, self-cleaning, non-secund, rosy-pink over a long period. The flowers produce an abundance of nectar and are attractive to hummingbirds in the landscape. The new plant is useful in the garden landscape, as a container plant or as a cut flower.

2 Drawing Sheets

Botanical designation: *Digitalis* x (*Digitalis* x *Isoplexis*).
Cultivar denomination: 'Flamingo'.

STATEMENT REGARDING PRIOR DISCLOSURES UNDER 37 CFR 1.77(B)(6)

The first non-enabling disclosures are a posting on Feb. 1, 2021 by Walters Gardens, Inc. on their website and a brief description and photograph in the "Walters Gardens 2021-2022 Catalog" first distributed on May 21, 2021. Information for these plants was obtained from the inventor. No plants of *Digitalis* 'Flamingo' have been sold, in this country or anywhere in the world nor has any disclosure of the new plant been made more than one year prior the filing date of this application, and such disclosure within one year was obtained either directly or indirectly from the inventor.

BACKGROUND OF THE INVENTION

The present invention relates to a new and distinct cultivar of hybrid plant, botanically known as *Digitalis* x (*Digitalis* x *Isoplexis*). The new intergeneric hybrid *Digitalis* x (*Digitalis* x *Isoplexis*) 'Flamingo' is the product of a planned breeding program conducted by the inventor at a wholesale perennial nursery in Zeeland, Mich., USA. The objective of the breeding program was to create novel intergeneric hybrid cultivars between *Digitalis* species and *Isoplexis* species with excellent flowers, foliage and habit.

The new intergeneric *Digitalis* hybrid was a planned cross between a proprietary selection of the seed cultivar *Digitalis purpurea* (not patented) as the female or seed parent times a proprietary, hybrid selection known only as 12-02-01 (not patented) as the male or pollen parent on Dec. 4, 2012 and later assigned the breeder code of 12-425-120. After further evaluation 'Flamingo' was selected as a single plant from among several hundred crosses between various forms of such *Digitalis* x (*Digitalis* x *Isoplexis*) hybrids and first asexually propagated by basal shoot cuttings in the fall of 2013 at the same wholesale perennial nursery in Zeeland, Mich. The new plant has since also been successfully asexually propagated by sterile shoot tip tissue culture. All of the resultant asexually propagated plants by cuttings and tissue culture have remained stable and reproduced true to type in successive generations.

SUMMARY OF THE INVENTION

Plants of the hybrid plant cultivar *Digitalis* x (*Digitalis* x *Isoplexis*) 'Flamingo' have not been observed under all possible environmental conditions. The phenotype may vary somewhat with variations in environment such as fertilizer, temperature, light intensity and photoperiod and plant growth regulators without, however, any variance in genotype.

The following traits in combination with one another have been repeatedly observed and are determined to be the unique characteristics of 'Flamingo':

1. Sturdy, upright and dense flowering habit;
2. High number of stiff basal branches extending bloom season from spring until frost;
3. Medium, open-faced, campanulate-formed, horizontal-facing, long-blooming, self-cleaning, non-secund flowers of rosy-pink;
4. Broad, dark-green, sparsely-pubescent, mostly-basal, serrate leaves.

Plants of the new *Digitalis* can be compared to the female parent, a proprietary selection of pink flowered *Digitalis purpurea* has longer, broader fertile flowers of lighter pale pink on shorter plants, the petal lobe apices are rounded and the flowering season is shorter. The female parent is also a biennial, whereas the new plant is a perennial in locations as warm as zone 8. The male parent has dark, glossy, glabrous foliage with less branching of the flower stems, and the flowers are apricot-yellow in color on darker stems.

Other closely comparable plants include, 'Berry Canary' U.S. Plant Pat. No. 27,607, 'Firebird' U.S. Plant Pat. No. 31,840, 'Flame' (not patented), ILLUMINATION® 'Pink' (not patented) and 'Pink Champagne' (not patented). 'Berry Canary' has a shorter habit and larger flowers of hot pink with light yellow throats with burgundy speckling. 'Firebird' has a slightly taller habit, and flowers of coppery-pink with soft orange throats having pinkish purple spotting. 'Flame' has a taller and broader habit with smaller flowers with a more orangish-red in the outside and peachy-orange in the inside with orangish-red spotting. ILLUMINATION® 'Pink' has petals with an outer surface color of hot pink with apricot undertones and the inner surface of creamy-melon and dark rose spotting. 'Pink Champagne' has fertile flowers that are soft pinkish-lavender to light pink on the outside with yellowish-cream center and reddish-burgundy spots, and the petal lobe apices are rounded.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants used in the drawings are two-year-old plants with a vernalization period of about 12 weeks, started in a greenhouse and later grown in a trial garden at a wholesale nursery in Zeeland, Mich. with supplemental fertilizer but without plant growth regulators.

DETAILED BOTANICAL DESCRIPTION

Figure 1:
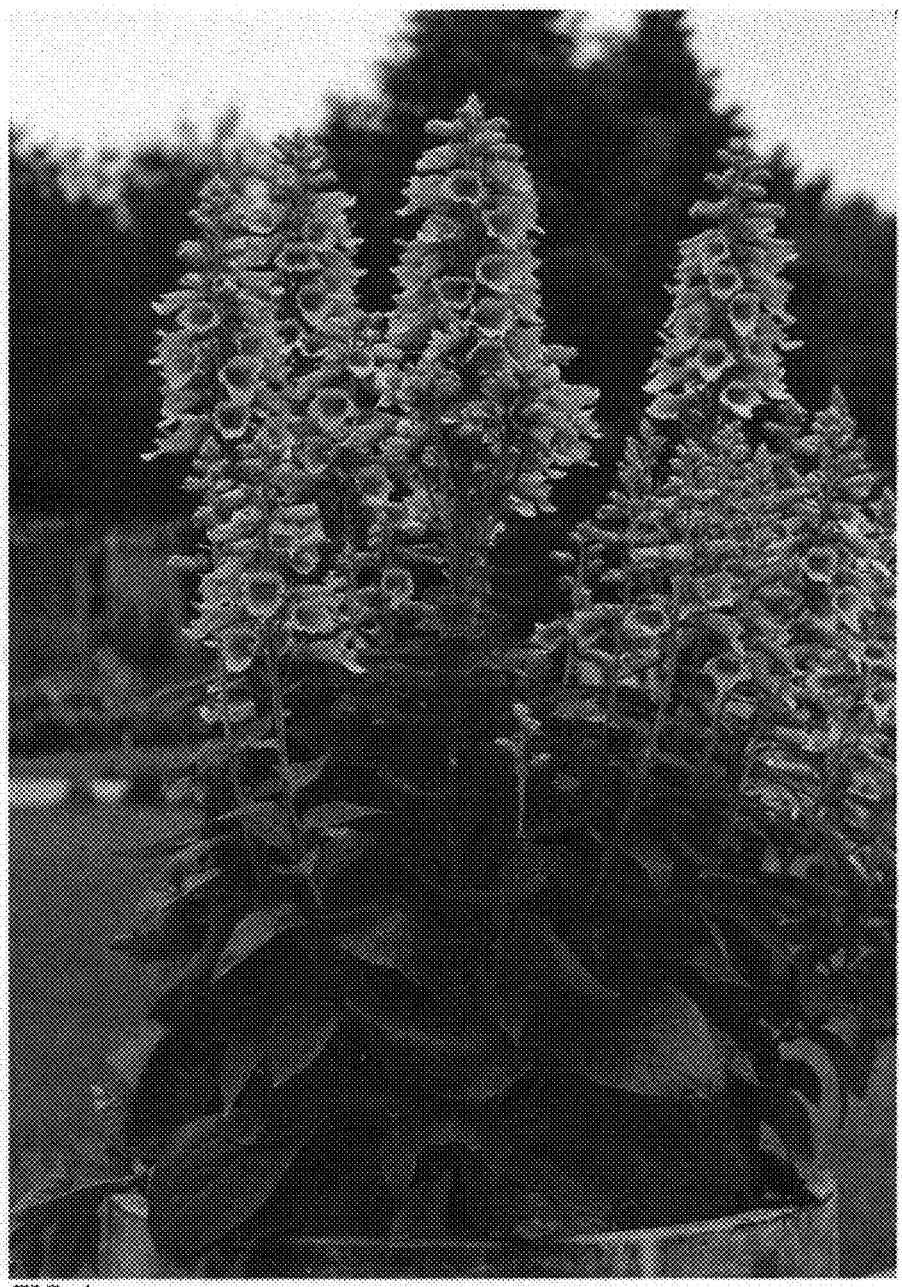
FIG. 1 shows the plant compact, dense, upright, flowering habit of a two-year-old plant.
Figure 2:
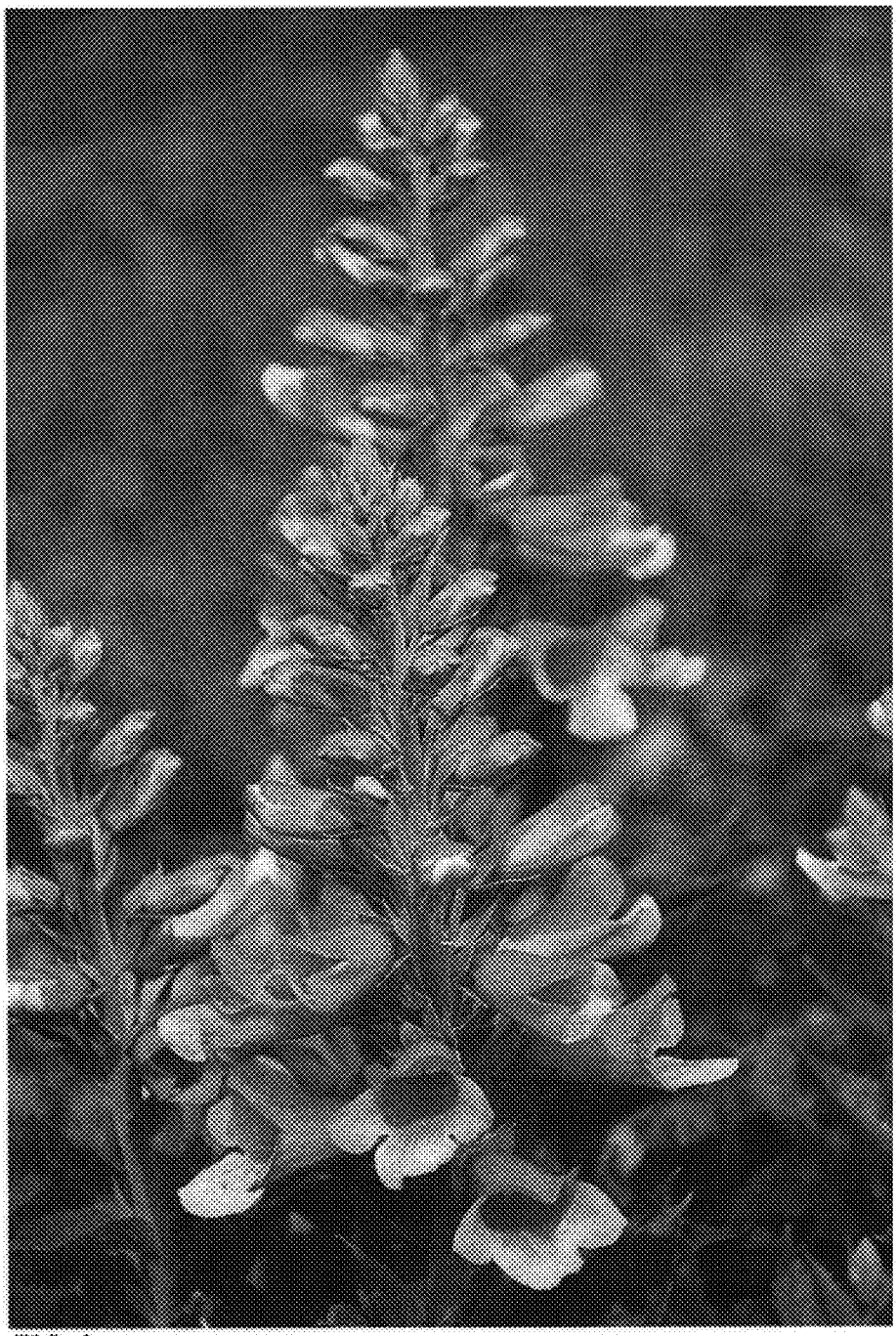
FIG. 2 shows a close-up of the flowers and buds on the scape.

The following descriptions and color references are based on the 2015 edition of The Royal Horticultural Society Colour Chart except where common dictionary terms are used. The new plant, 'Flamingo', has not been observed under all possible environments. The phenotype may vary slightly with different environmental conditions, such as temperature, light, fertility, moisture and maturity levels, but without any change in the genotype. The following observations and size descriptions are of two-year-old plants in the greenhouses of a nursery in Zeeland, Mich. with supplemental fertilizer and water as needed.

Parentage: Female, or seed parent an unnamed and unreleased selection of pink flowering form of *Digitalis purpurea*; male, or pollen parent an unreleased, proprietary, hybrid selection known by the breeder code 12-02-01 which is a hybrid between *Digitalis ambigua* times *Isoplexis canariensis;*

Propagation method: Shoot tip cuttings and sterile shoot tip plant tissue culture division.

Root description: Fine, freely branching; color creamy-white, nearest RHS 15D;

Time to initiate roots from tissue culture: About two weeks;

Crop time: Under normal cool spring growing conditions of 12° to 15° C., finished flowering plants can be obtained in about 8 to 10 weeks from a vernalized 25 mm plug;

Plant vigor: Very good;

Plant habit: Perennial, winter hardy from at least USDA zone 8 through 10 but capable of growing in colder regions as an annual; upright and dense; leaves basally whorled, cauline dextrorse to alternate and tightly arranged; with branching on nearly every node below individual flowers;

Main stem: Stiff and erect; about 75.0 cm long and 1.7 cm diameter at base; densely puberulent; cylindrical with basal portion having ridges extended from central leaf veins; length of ridges extends to next lower leaf directly below; with basal branches and axillary branches;

Main stem and branch color: Nearest RHS 146D and portions receiving higher light exposure moderately to lightly blushed nearest RHS N186C;

Nodes: About 40 per main stem before unbranched flowers; average about 11.0 mm apart, greater internode spacing distally; spacing of flowers of main stem about 4.0 mm;

Node color: Nearest RHS 146D with portions receiving higher light exposure moderately to lightly blushed nearest RHS N186C;

Branches: Outwardly in proximal portion, then upright next to main stem; to about 24 cm long and 8.0 mm diameter; densely puberulent; about fifteen main branches per plant from lower nodes and 12 branches in upper nodes below individual flowers; color and blushing same as main stem;

Foliage: Basally whorled and ovate; cauline dextrorse to alternate and lanceolate; sessile; acute apex and attenuate sessile base; very lightly puberulent on both adaxial and abaxial surfaces; serrate and ciliolate margin; slightly lustrous adaxial, slightly lustrous to matte abaxial;

Leaf size: Basal to about 20.0 cm long at base and 11.7 cm wide at widest point near base, cauline to about 14.5 cm long and 7.0 cm wide, decreasing distally; about 40 leaves per main stem below initial flowers;

Leaf blade color: Basal and cauline adaxial nearest RHS NN137A, basal and cauline abaxial nearest RHS 147B;

Veins: Pinnate; puberulent abaxial and sparsely puberulent to glabrous adaxial; costate on abaxial and slightly impressed adaxial;

Vein color: Adaxial midrib and proximal primary veins nearest RHS 145A, secondary and distal veins nearest RHS NN137A; abaxial midrib and proximal primary veins between RHS 145C and RHS 148C, proximal primary veins nearest RHS 146C, secondary veins and distal primary veins nearest RHS 137B;

Flower: Single; perfect; complete; campanulate; zygomorphic; total corolla average size 52.0 mm long and face opening to 30.0 mm across and 22.0 mm tall, with basal 35.0 mm of corolla tube fused and to about 20.0 mm wide and 14.0 mm tall at fusion; with four main lobes, two side lobes smallest and nearly perpendicular to upper and lower lobes; two side lobes about 9.0 mm wide at fusion and 9.0 mm long from fusion with broadly acute apex and micro-ciliolate margin; upper lobe about 21.0 mm wide at fusion and 10.0 mm long beyond fusion, slightly reflexed, with rounded micro-ciliolate apex; lowest lobe about 18.0 mm wide at fusion and 16.0 mm long beyond fusion, apex typically rounded and micro-ciliolate; speckling absent on adaxial petal surfaces and dorsal abaxial surface; speckling present on abaxial lowest lobe and side lobes in spots between 0.1 mm diameter and 0.3 mm diameter; sparsely puberulent to glandular on abaxial surfaces and pubescent on adaxial surfaces of middle portion of lower lobe; upper lobe and side lobes glabrous on adaxial surface; not persistent, self-cleaning; produces large amount of nectar;

Flower number: To about 70 per main stem, to about 39 per lateral lower branch and 5 per lateral upper branch;

Flower bud: Oblong tubular; to about 32.0 mm long and 14.0 mm wide near apex and about 9.0 mm tall near apex, constricting in basal 5.0 mm to about 4.0 mm diameter; apex and base rounded;

Flower bud color: Dorsal portion nearest a blend between RHS 186C and RHS 186B, side portions nearest RHS 186D with undertone of nearest RHS 18C, ventral portion variable with between RHS 186C and RHS 186B distally and proximally nearest RHS 18C with overtone of nearest RHS 186C;

Flower color: Varies with maturity; shortly after opening — ventral abaxial between RHS 72D and RHS NN74D, dorsal abaxial between RHS 70B and RHS 72C, and adaxial distally between RHS 72D and RHS NN74D with undertone and blotches about 1.0 mm diameter of nearest RHS 27D and adaxial central and proximally nearest on upper portion, lower portion middle between RHS 72D and RHS NN74D with blotches of RHS 27D about 1.0 mm and speckles in the center of blotches nearest RHS 187B; at pollen dehiscence about five days after opening — abaxial dorsal between RHS 72D and RHS NN74D with undertones of nearest RHS 186D, abaxial ventral proximally between RHS 72D and RHS NN74D with undertones of nearest RHS 70C and distally nearest RHS NN74D with undertones of nearest RHS 186D, adaxial upper lobe nearest a blend between RHS 70B and RHS 186D with midrib nearest RHS 162C, side lobes between RHS 70B and RHS 70C with blotches nearest RHS 18C, lower lobe nearest RHS 70B with blotches nearest 18D distally and proximally with a 10 mm patch of nearest RHS 158A and speckles in the patch of nearest RHS N79B, basal 5 mm of adaxial and abaxial corolla tube nearest RHS 145D;

Inflorescence: Average size main unbranched stem portion to about 39.0 cm long and 8.5 cm wide;

Flower bract: Lanceolate; sharply acute apex and truncate to rounded sessile base; margin finely serrated proximally and ciliolate proximally and distally; adaxial and abaxial finely puberulent; to about 40.0 mm long and 18.0 mm across near base, decreasing distally;

Flower bract color: Adaxial nearest RHS 137A, abaxial nearest RHS 147B;

Natural flowering season: Early summer through frost;

Flower longevity: Individual flowers on plant lasting about 7 to 10 days; main flower spike stays in flower for at least three months under ideal conditions;

Fragrance: None detected;

Sepals: Five; persistent; lanceolate; acute apex, truncate base, entire and micro-ciliolate margin; micro-puberulent abaxial and adaxial; about 18.0 mm long and 8.0 mm across at middle, decreasing in distal flowers;

Sepal color: Adaxial nearest a blend between RHS 147B and RHS 138A, abaxial RHS 147C;

Peduncle: Strong, erect; puberulent; to about 75.0 cm long and 9.0 mm in diameter below first flowers;

Peduncle color: nearest RHS 146D and portions receiving higher light exposure moderately to lightly blushed nearest RHS N186C;

Pedicel: Puberulent; cylindrical; erect to 60 degree angle above horizontal at flower anthesis; to 21.0 mm long and 2.0 mm diameter, decreasing with distal flowers;

Pedicel color: Nearest RHS 146C;

Gynoecium: Single; about 38.0 mm long;

*Style*.—Arcuate along adaxial upper lobe; lustrous; about 26.0 mm long and gradually tapering from ovary to stigma to about 1.0 mm diameter; color in young flower nearest RHS 155C and on mature flower developing light blush distally toward stigma nearest RHS N186C toward ovary.

*Stigma*.—Bifid in distal 0.5 mm; to about 1.0 mm long and about 0.5 mm wide; color nearest RHS 4D.

*Ovary*.—Superior; puberulent to glandular; lustrous; long, conical, apex tapering to meet style, base truncate; about 10.0 mm long and 5.0 mm across at base; color nearest RHS 144A.

Androecium: Four, didynamous; further extending set dehiscing first;

*Filaments*.—Four; cylindrical with basal portion flattened and adnate along inside of corolla tube; basal 13.0 mm on shorter filaments and 8.0 mm on longer filaments adnate to corolla; about 25.0 mm and 28.0 mm long and 1.0 mm diameter at base; color nearest RHS NN155B.

*Anther*.—Dorsifixed; folded in middle prior to dehiscence; each half about 4.0 mm long and each half about 2.0 mm across; color prior to dehiscence between RHS 11B and RHS 11C.

*Pollen*.—Abundant, dust-like; color nearest RHS 158B.

Fruit: Mature seed pods rarely produced;

Seed: Viable seed production has not yet been observed;

Disease and pest resistance or tolerance: 'Flamingo' is not normally bothered by rodents or deer in the landscape. Disease or pest resistance beyond that typical of other *Digitalis* hybrids has not been noted. The new plant performs best in full sun with good drainage and regular watering. Hardiness: the new plant is winter hardy to approximately USDA zone 8, but requires a vernalization period for best flower production.

It is claimed:

1. A new and distinct cultivar of *Digitalis* hybrid plant named 'Flamingo' as illustrated and described.

* * * * *